United States Patent
Hayashi et al.

(10) Patent No.: US 8,535,615 B2
(45) Date of Patent: Sep. 17, 2013

(54) RADICAL STERILIZATION APPARATUS

(75) Inventors: Nobuya Hayashi, Saga (JP); Saburoh Satoh, Saga (JP)

(73) Assignee: Saga University, Saga (JP)

( * ) Notice: Subject to any disclaimer, the term of this patent is extended or adjusted under 35 U.S.C. 154(b) by 988 days.

(21) Appl. No.: 11/989,433

(22) PCT Filed: Jul. 28, 2005

(86) PCT No.: PCT/JP2005/013858
§ 371 (c)(1),
(2), (4) Date: Mar. 6, 2009

(87) PCT Pub. No.: WO2007/013160
PCT Pub. Date: Feb. 1, 2007

(65) Prior Publication Data
US 2009/0304562 A1 Dec. 10, 2009

(51) Int. Cl.
*A61L 2/14* (2006.01)
(52) U.S. Cl.
USPC ..................... 422/292; 422/186.04
(58) Field of Classification Search
USPC ............ 422/22, 23, 28, 292, 186.04
See application file for complete search history.

(56) References Cited

U.S. PATENT DOCUMENTS 5,603,895 A * 2/1997 Martens et al. .................. 422/23
5,633,424 A * 5/1997 Graves et al. .................... 422/22
6,149,878 A * 11/2000 Jacob et al. ............... 422/186.04

FOREIGN PATENT DOCUMENTS

| JP | 07-018467 | 1/1995 |
| JP | 10-099415 | 4/1998 |
| JP | 10-319071 | 12/1998 |
| JP | 11-501530 A | 2/1999 |
| JP | 2002-510316 A | 4/2002 |

OTHER PUBLICATIONS

International Search Report issued Oct. 11, 2005 for corresponding PCT Application No. PCT/JP2005/013858.
Hayashi, N. et al. "Sterilization Characteristics for Medical Equipment's using Low-Pressure Radio Frequency Oxygen/Water Plasma" Plasma Science Symposium 2005/The 22nd Symposium on Plasma Processing, Jan. 26, 2005, pp. 691 & 692.

* cited by examiner

*Primary Examiner* — Sean E Conley
(74) *Attorney, Agent, or Firm* — Rader, Fishman & Grauer PLLC

(57) ABSTRACT

To provide a radical sterilization apparatus which can generate hydroxy (OH) radical and oxygen (O) radical at a high density to thereby surely and economically sterilize a subject to be treated. While maintaining a storage unit in which a medical instrument is stored at a low pressure by using a low pressure-maintaining unit, vapor is supplied form a vapor-supplying unit into the storage unit. Then, oxygen in this vapor is converted into radicals by a radical-forming unit to give hydroxy (OH) radical and oxygen (O) radical. Thus, the hydroxy radical and the oxygen (O) radical can be maintained each as a single radical over a long period of time and can be generated at a high density, which makes it possible to surely and economically sterilize the medical instrument.

9 Claims, 6 Drawing Sheets

RADICAL STERILIZATION APPARATUS

TECHNICAL FIELD

The present invention relates to a radical sterilization apparatus for sterilizing a subject to be treated, such as a medical instrument or the like, with hydroxy (OH) radicals, and more particularly relates to such a radical sterilization apparatus for sterilizing the subject to be treated by the hydroxy (OH) radicals generated from water vapor.

BACKGROUND OF ART

There are plasma sterilization apparatuses as background arts which are disclosed in Japanese Laid-Open Patent Publication (KOKAI) No. H10-099415A (first background art) and Japanese Laid-Open Patent Publication (KOKAI) No. H07-018461A (second background art), and these background arts are shown in FIGS. 5 and 6 in schematic structural cross-sectional views, respectively.

In FIG. 5, this first background art plasma sterilization apparatus includes: a first chamber 114 having a plasma generation unit 112 in which plasmas are generated under an atmospheric pressure; a second chamber 118 featuring a pressure-resistance structure, in which subjects 136 to be treated can be placed; and joint pipes 124 which connect the first and second chambers 114 and 118 to each other in openable and closable manners, and each of which has an on-off valve 120 for controlling a flow of gas, containing sterilization factors, fed from the first chamber 114 to the second chamber 118, and a compressor 122 formed as a pressurized unit. A pressure regulating unit 116 is connected to the second chamber 118 so as to maintain a pressure in an interior of the second chamber 118 constant by feeding the gas thereto and exhausting the gas therefrom. In the plasma generation unit 112, at least one part of a mixture of gas and liquid can be ionized by using a pulse power source, and the ionized mixture thus obtained forms the sterilization factors.

Like this, in addition to the second chamber 118 for sterilizing the subjects 136 to be treated, there is the first chamber 114 for storing the sterilization factors, and both the first and second chambers are connected to each other by the joint pipes 124 having the on-off valves 120, whereby it is possible to carry out not only the storage of the sterilization factors necessary for the sterilization but also a pretreatment of the subjects to be treated, such as a drying treatment and so on, and whereby it is possible to efficiently carry out an effective sterilization treatment in that the subjects to be treated can be contacted with a large amount of the sterilization factor in a short time.

Also, in FIG. 6, according to the second background art plasma sterilization apparatus, a lid 202 is opened, and a vessel 218 to be sterilized is put into a vacuum container 201. Then, the lid 202 is closed, and the vacuum container 201 is exhausted by a vacuum pump 204 until a sufficiently lower pressure is obtained than a pressure at which a plasma is generated in the vacuum container. Subsequently, a gas is introduced from a gas source 214 into the vacuum container at a suitable flow rate, and a valve 215 is regulated so that the pressure suiting the plasma is maintained. On the other hand, the vacuum pump 204 is continuously operated so that the pressure is stabilized, and thereafter a high frequency power is applied from a high frequency power source 212 to an electrode 208 to thereby generate the plasma in the vessel 218. After the plasma is maintained over a time during which the sterilization is sufficiently carried out, the application of the high frequency power is stopped, resulting in a completion of the sterilization of the vessel 218. Also, when the application of the high frequency power is stopped, the introduction of the gas is simultaneously stopped, and the operation of the vacuum pump is stopped after the exhaust is momentarily continued. Then, an atmosphere introduction valve 217 is opened to thereby introduce an atmosphere into the vacuum container. Thereafter, the lid 202 is opened, and the vessel 218 is took out.

Patent Document 1: Japanese Laid-Open Patent Publication (KOKAI) No. H10-099415

Patent Document 2: Japanese Patent Publication No. 3209944

DISCLOSURE OF THE INVENTION

Problems to be Resolved by the Invention

Due to the fact that the aforesaid first background art plasma sterilization apparatus is constructed as stated above, although the plasma is generated in the first chamber 114 under the atmospheric pressure to thereby generate oxygen plasma, under the atmospheric pressure, the oxygen plasma is immediately bonded to gases, for example, oxygen, hydrogen, nitrogen and so on, existing in the first chamber 114, and thus the oxygen plasma per se cannot exist as it stands so that there is a problem that a sufficient sterilization effect cannot be obtained.

Also, the aforesaid second background art plasma sterilization apparatus is intended to sterilize the vessel 218 which is the subject to be sterilized, but oxygen plasma cannot be generated as a simple at a high density due to the fact that the plasma P is generated by the introduction of a plasma generation gas comprising a mixture of an inert gas and a reactive gas, and thus there is a problem that the vessel 218, which is the subject to be sterilized, cannot be surely subjected to the sterilization treatment. In this second background art, the sterilization means a reduction of a microorganism population by microbiologically killing microorganism, which is considerably different from extinction or elimination of all the microorganism from a substance to be sterilized and an environment thereof.

Furthermore, there is another background art plasma sterilization apparatus in which hydrogen peroxide is used as a raw gas to generate hydroxy (OH) radicals, and in which sterilization is carried out by using a sterilizing ability of the hydroxy (OH) plasma, but, due to the fact that hydrogen peroxide is a liquid at a normal temperature and a normal pressure, a structure of the apparatus and a running manner (pressure regulation) thereof are complicated in a case where the liquid is introduced into a plasma container having a low pressure, and hydrogen peroxide per se is expensive. Thus, there is a problem that both a cost of the apparatus per se and a running cost therefor become larger.

Especially, when the raw gas is hydrogen peroxide, a density of hydrogen peroxide should be on the order of 85%. Accordingly, the toxicity of hydrogen peroxide is very strong, and thus the apparatus has problems that a handling involves some risk, and that an operator may be poisoned with the remaining hydrogen peroxide gas after the sterilization treatment. Before the remaining hydrogen peroxide gas can be removed, a decomposition apparatus for decomposing the hydrogen peroxide gas must be provided in addition to the plasma sterilization apparatus, and thus there is another problem that a system arrangement becomes complicated and large-sized.

Also, in a case where the sterilization treatment is carried out by switching a pressure in a container for storing a subject to be treated which is to be sterilized, from one of a high vacuum state and a low vacuum state to the other state, when hydrogen peroxide which is the liquid state is used as the raw gas, there are problems that an operation of the aforesaid pressure regulation is very difficult, and that it takes a long time to uniformly diffuse hydroxide plasma in the container.

The present invention is achieved to resolve the aforesaid problems, and provides a plasma sterilization apparatus in which not only can hydroxy (OH) radicals and oxygen (O) radicals be generated at a high density to surely and inexpensively sterilize subjects to be treated, but also it is possible to insure security of operators.

Means for Solving the Problems

A radical sterilization apparatus according to the present invention comprises: a storage means that stores a subject to be treated, being to be subjected to a sterilization process, and that includes an airtight container; a low air pressure maintaining means for maintaining a pressure in the aforesaid storage means at a low pressure state; a water vapor gas production means that is in commutation with the aforesaid storage means, and that produces water vapor gas by vaporizing a water introduced thereinto; and a radical generation means that generates hydroxy (OH) radicals and oxygen (O) radicals by ionizing hydrogen oxide of the aforesaid water vapor gas, an electrode being at least stored in the storage means, the ionization of hydrogen oxide being carried out by causing electric discharge by applying an electric current to the electrode in a water vapor ambiance defined by supplying the water vapor gas to the storage means.

Like this, in the present invention, since the air pressure in the storage means storing the subject to be treated is maintained to be low, and since the water vapor gas is supplied from the water vapor gas production means to the storage means so that hydrogen oxide of the water vapor gas is ionized by the radical generation means to thereby generate hydroxy (OH) radicals and oxygen (O) radicals, the hydroxy (OH) radicals and oxygen (O) radicals per se can last as they stand over a long period of time, and can be generated at a high density, so that it is possible to surely and inexpensively sterilize the subject to be treated.

Also, in the radical sterilization apparatus according to the present invention, if necessary, an air pressure in the water vapor gas production in the water vapor gas production means is higher than an interior air pressure in the airtight container of the storage means, but it is lower than an atmospheric pressure. Like this, in the present invention, since the water vapor gas production means is arranged so that the water vapor gas is produced at the higher air pressure than the interior pressure in the storage means, a large amount of water vapor gas is quickly produced at the lower pressure than the atmospheric pressure, and the produced water vapor gas is smoothly introduced into the storage means having a further low pressure, so that the radical generation means surely and smoothly carries out an electric discharge in a low pressure ambiance defined by the introduced water vapor gas. Thus, it is possible to more efficiently generate hydroxy (OH) radicals and oxygen (O) radicals.

Also, in the radical sterilization apparatus according to the present invention, if necessary, the water vapor gas production means is integrally formed with and identified with the airtight container of the storage means. Like this, in the present invention, since the water vapor gas production means is integrally formed with and identified with the airtight container of the storage means, resulting in a simplified structure of the apparatus, the hydroxy (OH) radicals and oxygen (O) radicals per se can last as they stand over a long period of time, and can be generated at a high density, so that it is possible to surely and inexpensively sterilize the subject to be treated.

Also, in the radical sterilization apparatus according to the present invention, if necessary, the radical generation means is arranged so that a low pressure glow discharge is generated by the electrode with an electrical current supplied thereto. Like this, in the present invention, since the radical generation means is arranged so that a low pressure glow discharge is generated by the electrode with the electrical current supplied thereto, the electrode of the radical generation means can carry out a volume discharge in the airtight container of the storage, and thus it is possible to high efficiently generate the hydroxy (OH) radicals and oxygen (O) radicals over the whole area of the airtight container.

Also, in the radical sterilization apparatus according to the present invention, if necessary, the radical generation means is driven so that the electrode is supplied with the alternating current at the frequency from 1 kHz to 10 kHz, and so that the alternating voltage from 7 kV to 13 kV is applied to the electrode 41. Like this, since the radical generation means is driven so that the electrode is supplied with the alternating current at the frequency from 1 kHz to 10 kHz, and so that the alternating voltage from 7 kV to 13 kV is applied to the electrode 41, the alternating current having the frequency from 1 kHz to 10 kHz can be supplied to the electrode so that it is possible to obtain resonance with water molecules (ions) of the water vapor gas, and the alternating voltage from 7 kV to 13 kV can be applied so that it is possible to surely and easily control a commencement of the electric discharge and a maintenance of the electric discharge in the water vapor ambiance. Thus, it is possible to increase a generation rate of the hydroxy (OH) radicals and oxygen (O) radicals. Especially, due to the fact that the applied voltage is from 7 kV to 13 kV, it is possible to easily control the commencement of the electric discharge and the maintenance of the electric discharge without a voltage-applying state of the electrode being not as a self-bias state, and thus it is possible to configure the electrode without being subjected to restrictions on a specific arrangement and a particular nature of the electrode.

Also, in the radical sterilization apparatus according to the present invention, if necessary, the liquid water is directly introduced into the low air pressure container by using a small flow-rate variable needle valve. Like this, in the present invention, since the liquid water is directly introduced into the low air pressure container by using the small flow-rate variable needle valve, it is possible to minutely and accurately adjust a production rate of the water vapor gas, and thus it is possible to efficiently carry out the generation of the hydroxy (OH) radicals and oxygen (O) radicals.

Also, in the radical sterilization apparatus according to the present invention, if necessary, the low air pressure maintaining means changes the pressure of the water vapor in the airtight container of the aforesaid storage means from 1 Pa to 1,000 Pa. Like this, in the present invention, since the low air pressure maintaining means changes the pressure of the water vapor in the airtight container of the aforesaid storage means from 1 Pa to 1,000 Pa, the hydroxy (OH) radicals and oxygen (O) radicals can surely penetrate into the subject to be treated, resulting in an improvement of the sterilization effect.

Also, in the radical sterilization apparatus according to the present invention, if necessary, the air pressure in the container of the water vapor gas production means is from 10 Pa to 10,000 Pa, the air pressure in the airtight container of the storage means is from 1 Pa to 1,000 Pa, and the respective air pressures of the water vapor gas production means and storage means are proportionally increased and reduced. Like this, in the present invention, since the water vapor gas production means is arranged so that the water vapor gas is produced at the higher air pressure (1 Pa→10 Pa, ..., 1,000 Pa→10,000 Pa) than the interior air pressure in the storage means, a large amount of water vapor gas is quickly produced at the lower pressure from 10 Pa to 10,000 Pa than the atmospheric pressure, and the produced water vapor gas is smoothly introduced into the storage means having a further low pressure from 1 Pa to 1,000 Pa, so that the radical generation means surely and smoothly carries out an electric discharge in a low pressure ambiance defined by the introduced water vapor gas of from 1 Pa to 1,000 Pa. Thus, it is possible to more efficiently generate hydroxy (OH) radicals and oxygen (O) radicals.

Also, in the radical sterilization apparatus according to the present invention, if necessary, the air pressure in the container is higher that that during the electric discharge during the water vapor gas production, and the production of water vapor and the generation of hydroxy (OH) radicals and oxygen (O) radicals are alternately carried out. Like this, in the present invention, since the air pressure in the container is higher that that during the electric discharge during the water vapor gas production, and since the production of water vapor and the generation of hydroxy (OH) radicals and oxygen (O) radicals are alternately carried out, it is possible to set respective optimum condition pressures on the generation of the water vapor gas and the generation of the hydroxy (OH) radicals and oxygen (O) radicals by the electric discharge, whereby it is possible to more efficiently carry out the generation of the hydroxy(OH) radicals and oxygen (O) radicals. Especially, when the water vapor production means is integrally formed with the airtight container of the storage means, it is possible to adjust the respective air pressures in the single airtight container on the generation of the water vapor gas and the generation of the hydroxy (OH) radicals and oxygen (O) radicals by the electric discharge, whereby it is possible to more efficiently carry out the generation of the hydroxy (OH) radicals and oxygen (O) radicals.

BRIEF EXPLANATIONS OF DRAWINGS

EXPLANATION OF REFERENCES

1 Storing Means
2 Low Pressure Maintaining Means
3 Water-Vapor Gas Generating Means
4 Radical Generating Means
5 Container-Interior Condition Controller Portion
6 Medical Instrument
21 Rotary Pump
22 Exhaust Pipe
23 Regulator Value
24, 34 Connector
31 Water Tank
32, 35 Supply pipe
32a, 32b Supply pipe
33 Small Flow-Rate Variable Needle Valve
34 Sealed Container
34a, 34b, 36a, 37a, 46a, 46b Sealed Portion
35 Discharge Pipe
36 Discharge Valve
41 Electrode
42 Power Supply Portion
43 Frequency Switching Portion
45 Wiring Leads
210 Vacuum Container
Q Virtual Central Axis

THE BEST MODE FOR EMBODYING THE INVENTION

First Embodiment of the Invention

Figure 1:
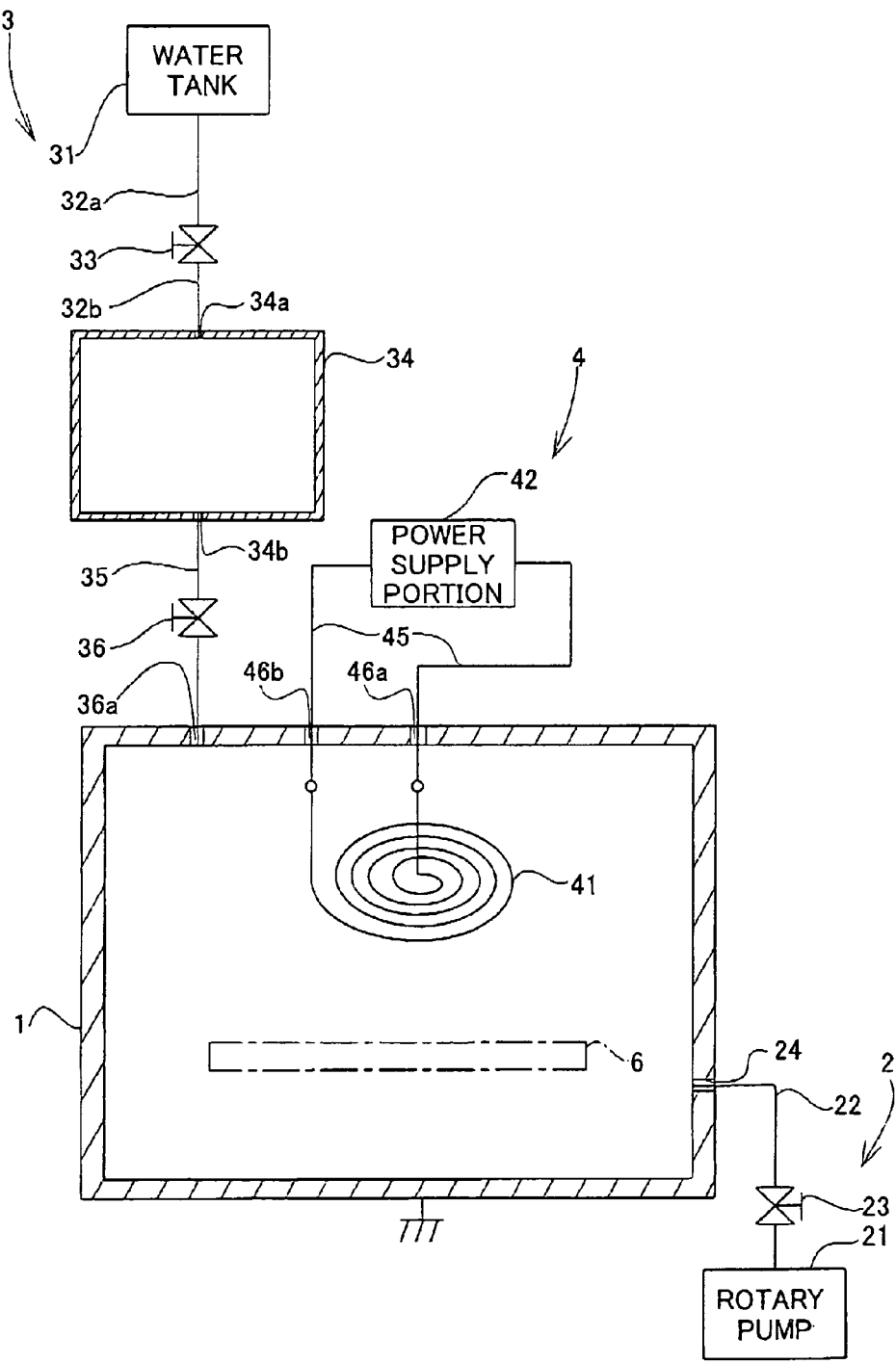
FIG. 1 is a schematic structural view of a radical sterilization apparatus according to a first embodiment of the present invention.

A radical sterilization apparatus according to a first embodiment of the present invention will now be explained based on FIG. 1 below. FIG. 1 is a schematic structural view of the radical sterilization apparatus according to the present embodiment.

In this drawing, the radical sterilization apparatus according to the present embodiment is a structure including: a storing means 1 comprising an airtight container for storing a medical instrument 6 which is a subject to be sterilized; a low air pressure maintaining means 2 for maintaining a pressure in the aforesaid storage means 1 at a low pressure state; a water vapor gas production means 3 which is in communication with the aforesaid storage means 1, and which produces water vapor gas by introducing a water thereinto; and a radical generation means 4 in which generates hydroxy (OH) radicals and oxygen (O) radicals by ionizing water molecules of the aforesaid water vapor by energizing an electrode 41, at least stored in the aforesaid storage means 1, with electric current.

The low air pressure maintaining means 2 is a structure including: a rotary pump 21 for exhausting air from the storage means 1; an exhaust pipe 22 communicated with and connected to each of the rotary pump 2 and the storage means 1; a regulator valve 23 provided at a middle of the aforesaid exhaust pipe 22 to regulate an amount of the exhausting air; and a connector 24 for airtightly connecting the aforesaid exhaust pipe 22 to a side wall hole of the storage means 1.

The water vapor gas production means 3 is a structure including: a water tank 31 for storing water; a small flow-rate variable needle valve 33 connected to the water tank 31 through the intermediary of a supply pipe 32a so as to produce water vapor gas in a low pressure state at a post-stage side; and a sealed container 34 connected to a post-stage side of the small flow-rate variable needle-valve 33 through the intermediary of a supply pipe 32b and connected to the aforesaid radical generation means 4 through the intermediary of a discharge pipe 35 having a discharge valve 36, so that water vapor gas, which is produced at the small flow-rate variable needle valve 33 from a small amount of water supplied from the supply pipe 32, is discharged and supplied to the radical generation means 4. The sealed container 34 is arranged so as to be connected to both the supply pipes 32 and 35 through the intermediary of sealed portions 34a and 34b.

The aforesaid radical generation means 4 is a structure including: an electrode 41 comprising an inductiuly-coupled type antenna formed by spirally winding an electrically conductive wire; a power supply portion 42 for supplying the electrode 41 with an alternating current; wiring leads 45 connecting between the power supply portion 42 and the electrode 41; and sealed portions 46a and 46b for airtightly sealing the side wall holes of the storage means 1, through which the wiring leads 45 pass. The radical generation means 4 is constituted so that hydroxy (OH) radicals and oxygen (O) radicals are generated from the water molecules of the water vapor by electrons moving in an impedance Z defined in a space between the electrode 41 and the grounded storage means 1.

Next, an operation of the radical sterilization apparatus according to the present embodiment based on the aforesaid structure will now explained. First, the regulator valve 23 is put into an open-state, and the rotary pump 21 is started to thereby exhaust air from the storage means 1 so that a given low pressure state, for example, from 1 Pa to 1,000 Pa, is created in the storage means 1. While the exhaust is continued by the regulator valve 23, the small flow-rate variable needle valve 33 of the water vapor gas production means 3 is opened, a small amount of water is supplied from the water tank 31 to the sealed container 34 through the intermediary of the supply pipe 32.

Since the aforesaid sealed container 34 is connected to the storage means 1, in which the low pressure state is maintained, through the intermediary of the supply pipe 35, a pressure state in the sealed container is controlled at a low pressure, for example, from 10 Pa to 10,000 Pa, which is lower than the atmospheric pressure due to the exhausting of the air from the storage means 1, and which is higher than the interior air pressure in the storage means 1, and thus, due to this low pressure, a water vapor is produced from a small amount of water supplied from the supply 32. The produced water vapor is supplied to the storage means 1 through the intermediary of the supply pipe 35, with the supplied amount of the water vapor being controlled by the discharge valve 36.

The electrode 41 is supplied with the alternating current from the power supply portion 42 of the radical generation means 4 on the condition that an oxygen gas pressure in the aforesaid storage means 1 reaches a given value (for example, from 1 Pa to 1,000 Pa, preferably, from 1 Pa to 10 Pa). The electrode 41 generates an electromagnetic wave due to the alternating current, and water molecules of the water vapor ($H_2O$) are ionized (ionization) due to the electromagnetic wave so that water molecule ions ($H_2O$) and electrons ($e^-$) are generated.

The generated electrons ($e^-$) are collided with atoms of the water vapor ($H_2O$) in the storage means 1 so that a high energy is exerted to the water vapor ($H_2O$), and thus hydroxy (OH) radicals and oxygen (O) radicals are generated. Like this, since the hydroxy (OH) radicals and oxygen (O) radicals are generated from the water vapor ($H_2O$) having the high energy, the plasma density is increased so that it is possible to obtain a large production amount of the hydroxy (OH) radicals and oxygen (O) radicals, with only the water vapor being used as a raw material in the low pressure state of the storage means 1 so that the hydroxy (OH) radicals and oxygen (O) radicals per se can last as they stand over a long period of time.

Especially, in order that the hydroxy (OH) radicals and oxygen (O) radicals to be generated has a maximum density (for example, $10^{10}$ $cm^{-3}$), the aforesaid radical generation means 4 should have a power supply frequency from 1 kHz to 10 IHz, the alternating current voltage applied to the electrode 41 should be 7 kV to 13 kV, and a discharge consumption power should be 50 W to 150 W. Furthermore, the storage means 1 should have an interior oxygen gas pressure of 3 Pa, and a flow rate of the oxygen gas should be 10 sccm (standard cc/min.)

Second Embodiment of the Invention

Figure 2:
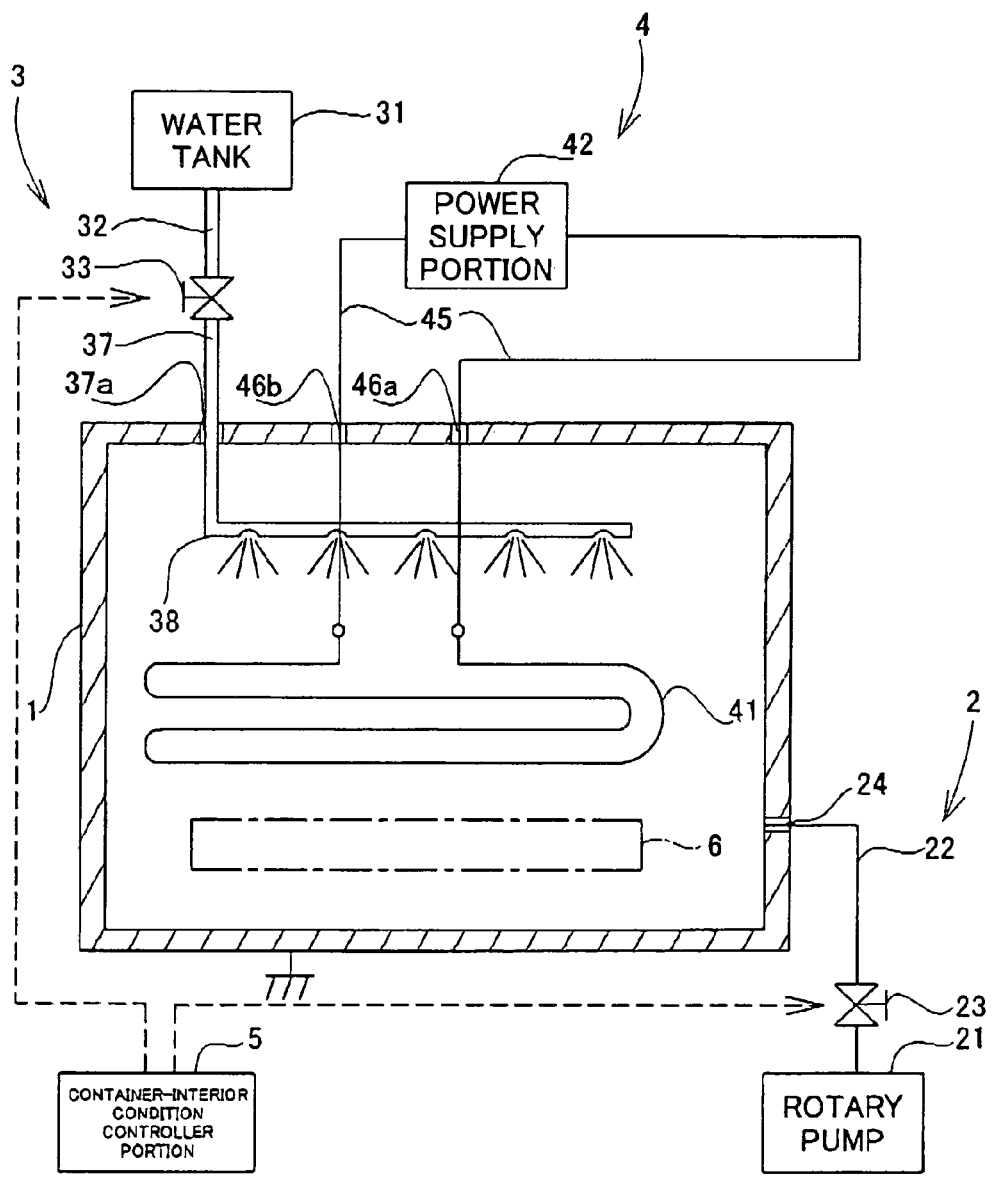
FIG. 2 is a schematic structural view of a radical sterilization apparatus according to a second embodiment of the present invention.
Figure 3:
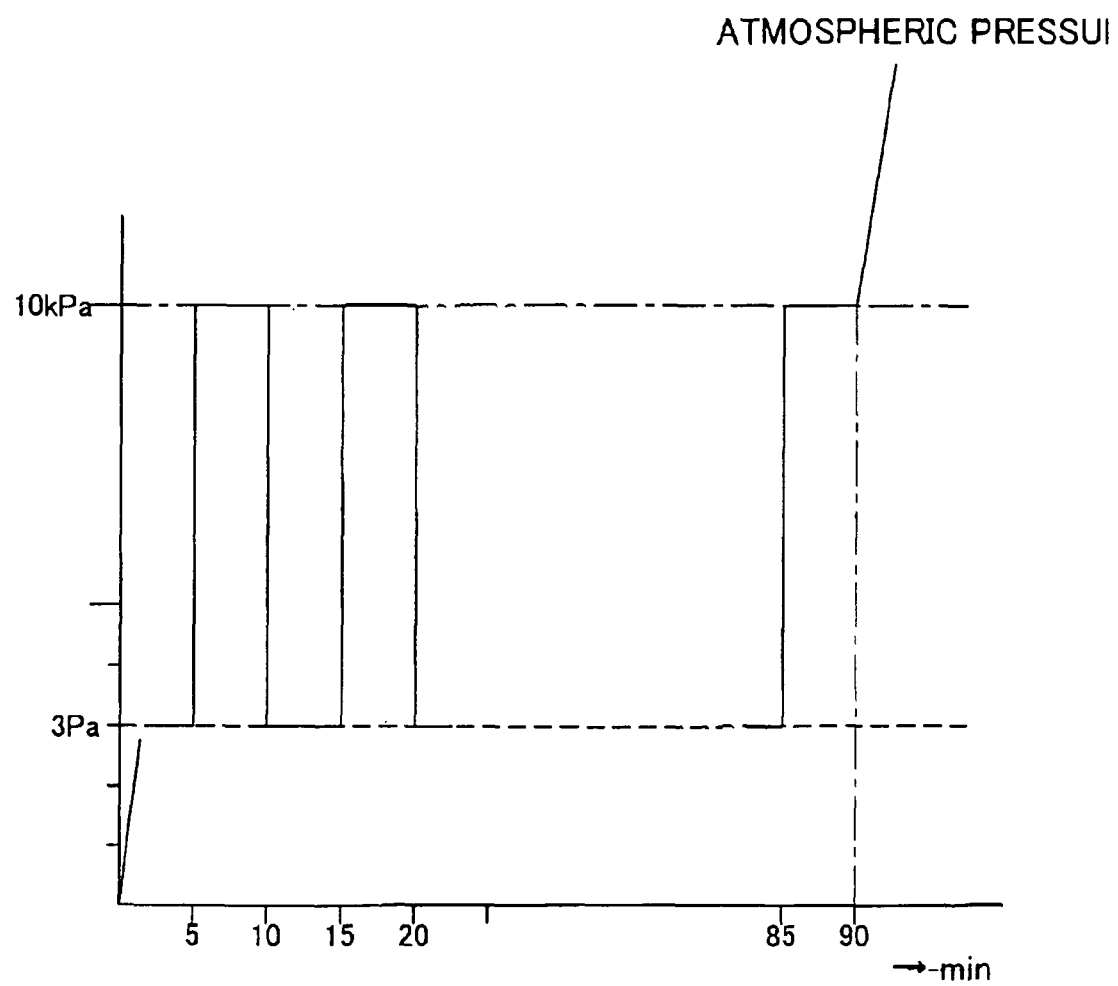
FIG. 3 is an operational timing chart of the radical sterilization apparatus shown in FIG. 2.

A radical sterilization apparatus according to a second embodiment of the present invention will now be explained based on FIGS. 2 and 3 below. FIG. 2 is a schematic structural view of the radical sterilization apparatus according to the present embodiment, and FIG. 3 is an operational timing chart of the radical, sterilization apparatus shown in FIG. 2.

In each of the aforesaid views, similar to the radical sterilization apparatus according to the aforesaid first embodiment, the radical sterilization apparatus according the present embodiment includes a storing means 1, a low air pressure maintaining means 2, a water vapor gas production means 3 and a radical generation means 4, but, the water vapor gas production means 30 in this structure (corresponding to 3 in the first embodiment) is different. The water vapor gas production means 30 is a structure including: a water tank 31 for storing water; a small flow-rate variable needle valve 33 connected to the water tank 31 through the intermediary of a supply pipe 32a and to the aforesaid storage means 1 through the intermediary of a discharge pipe 37 so as to produce water vapor gas in a low pressure state in the storage means 1; and a diffusion unit 38 for uniformly diffusing and spreading the produced water vapor gas in the storage means 1.

An opening degree of the small flow-rate variable needle valve 33 is adjusted by an additionally provided container-interior condition controller portion 5 so that a contact area between the water and the low pressure zone in the storage means 1 forming a post-stage side is finely adjusted, with an introduction amount of the water being finely adjusted so that a production rate of the water vapor is accurately controlled. Also, the aforesaid container-interior condition controller portion 5 can control an air pressure in the storage means 1 within a range between 1 Pa and 1,000 Pa by adjusting a suction rate of the rotary pump 21 with an opening degree of the regulator valve 23 of the low air pressure maintaining means 2.

In the case where an opening degree of the small flow-rate variable needle valve 33 is fixed at a given value, after the pressure of the water vapor in the storage means 1 is changed from 1 Pa to 1,000 Pa by adjusting the suction rate of the rotary pump 21, an amount of water introduced by the aforesaid container-interior condition controller portion 5 is adjusted from 0.01 sccm to 10 sccm so that a supply amount of water vapor can be adjusted from 10 sccm to 1,000 sccm.

Next, an operation of the radical sterilization apparatus according to the present embodiment based on the aforesaid structure will now explained. First, the regulator valve 23 is controlled so as to be fully opened based on the control of the container-interior condition controller portion 5, and then the rotary pump 21 is driven. Also, by driving the rotary pump 21, the pressure in the storage means 1 is reduced to a given low air pressure (for example, 1 Pa). Then, in this low pressure state, the small flow-rate variable needle valve 33 of the water vapor gas production means 3 is finely adjusted to be opened so that a water vapor is produced from the water supplied from the water tank 31, and the produced water vapor is controlled so as to be uniformly distributed in a whole interior of the storage means 1 by the diffusion unit 38.

Like this, under the condition that the water vapor is uniformly diffused and distributed in the storage means 1, the electrode 41 is supplied with the alternating current at the frequency from 1 kHz to 10 kHz from the power supply portion 42, and the alternating voltage from 7 kV to 13 kV is applied to the electrode 41.

Further, by the container-interior condition controller portion 5, the respective opening degrees of the regulator valve 23 of the low air pressure maintaining means 2 and the small flow-rate variable needle valve 33 of the water vapor gas production means 3 are adjusted so that the water vapor pressure of 1 Pa is created in the storage means 1, and an introduction of the water vapor gas at the flow rate of 10 sccm into the storage means 1 is continued over a period of 5 min. Then, the water vapor pressure of 1,000 Pa is created in the storage means 1, and an introduction of the water vapor gas at the flow rate of 10,000 sccm into the storage means 1 is continued over a period of 5 minutes. both the introductions are alternately and cyclically carried out over a period of 90 minutes (see: FIG. 3).

Like this, since both the change of the water vapor gas pressure from 1 Pa to 1,000 Pa and the change of the water vapor gas flow rate from 10 sccm to 1,000 sccm are switched at an interval of 5 minutes, the hydroxy (OH) radicals and oxygen (O) radicals can penetrate into minute sections of medical instruments, under-surfaces of set medical instruments and so on, and thus it is possible to surely and easily sterilize the medical instruments over the whole area thereof.

Third Embodiment of the Invention

A radical sterilization apparatus according to a third embodiment of the present invention will now be explained based on FIG. 4 below. FIG. 4 is schematic structural cross-sectional and longitudinal-sectional views of a radical sterilization apparatus according to a third embodiment of the present invention.

Figure 4A:
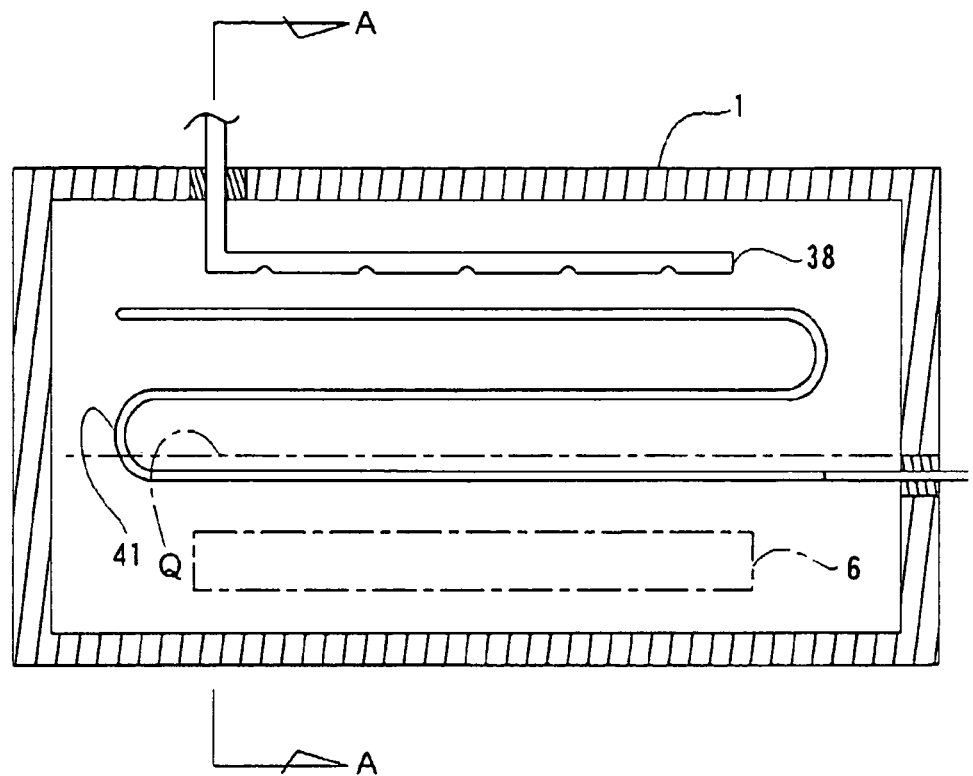
FIG. 4 is schematic structural cross-sectional and longitudinal-sectional views of a radical sterilization apparatus according to a third embodiment of the present invention.
Figure 4B:
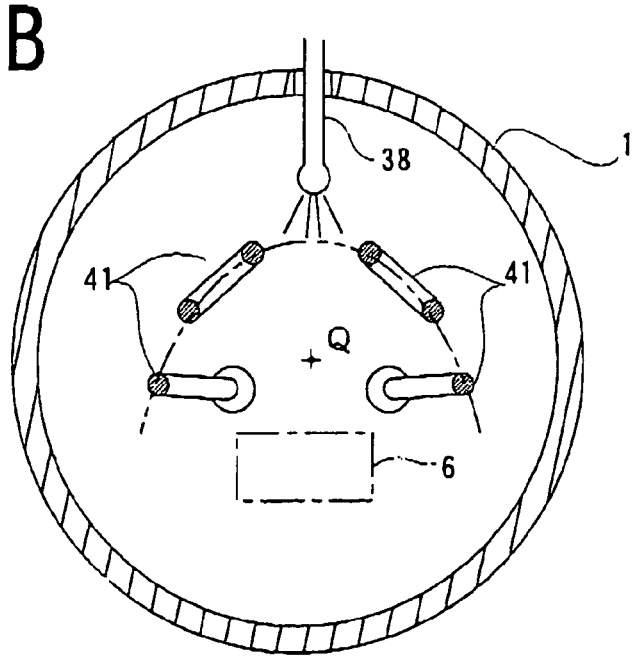
Figure 5:
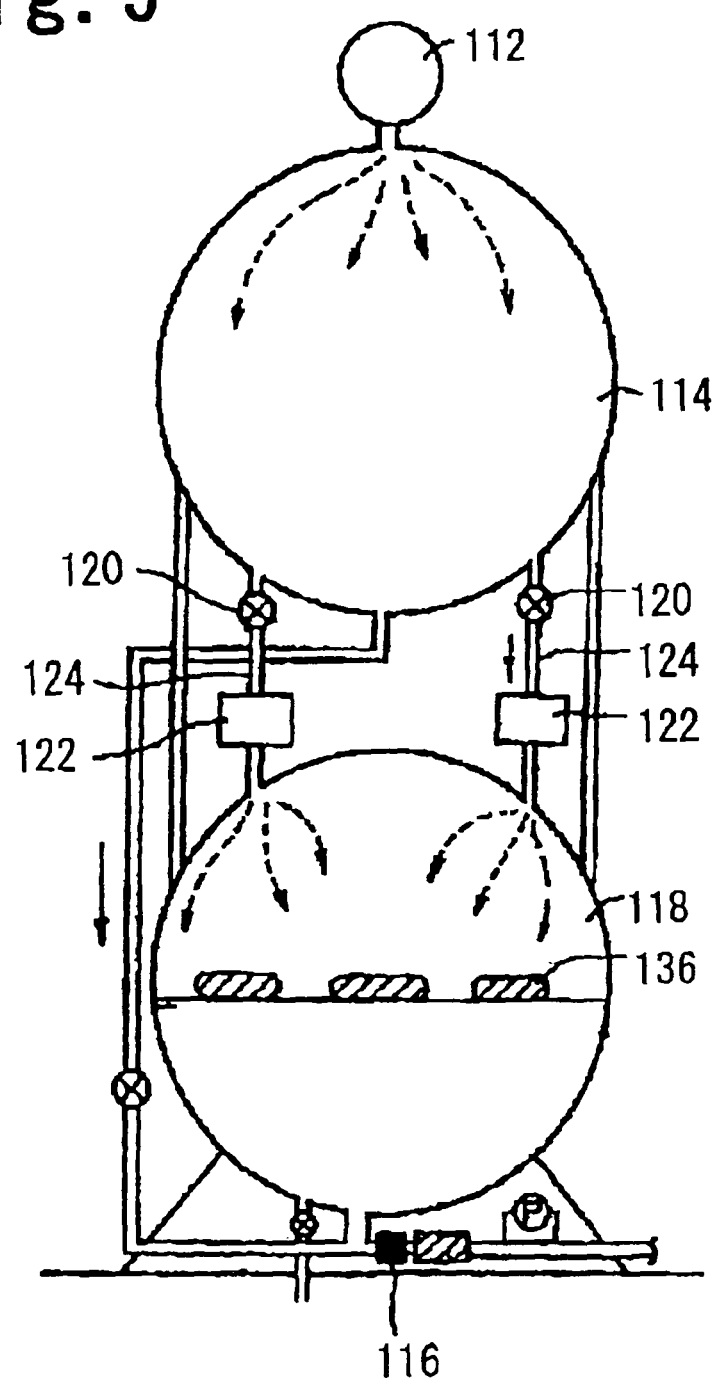
FIG. 5 is a schematic sectional structural view of a conventional radical sterilization apparatus.
Figure 6:
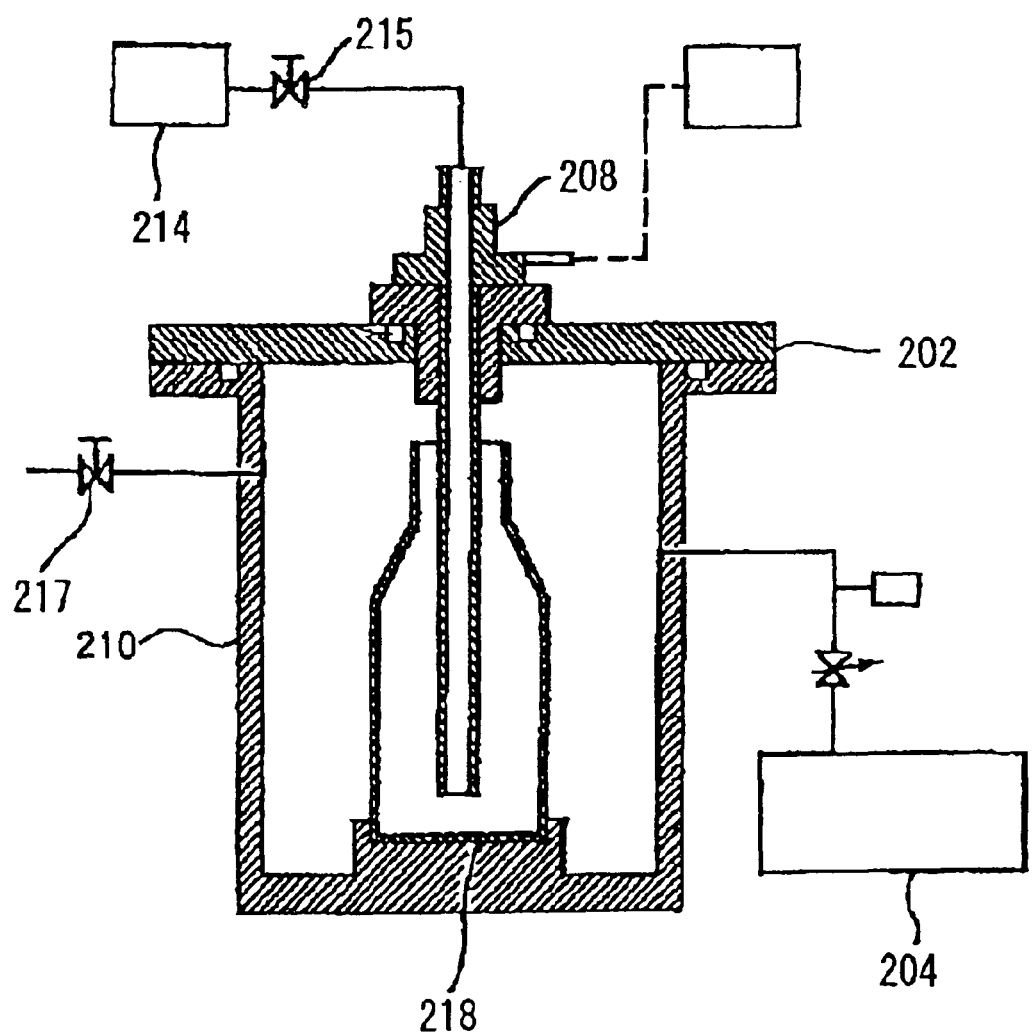
FIG. 6 is a schematic sectional structural view of a conventional radical sterilization apparatus.

In these drawings, similar to the radical sterilization apparatuses according to the aforesaid first and second embodiments, the radical sterilization apparatus according the present embodiment commonly includes a storing means 1, a low air pressure maintaining means 2, a water vapor gas production means 3 and a radical generation means 4, but an arrangement of an electrode 41 in the aforesaid radical generation means 4 is different. The electrode 41 includes linear antenna lines which are formed by bending a cylindrical tube many times so as to be in parallel to a virtual central axis Q of the storage means 1 (see: FIG. 4(A)), and the linear antenna lines are arranged to describe a circular arc around the aforesaid central axis Q (see: FIG. 4(B)). A diffusion unit 38 is arranged between the electrode 41 and the inner wall of the storage means 1, and water vapor gas, which is diffused and distributed from the diffusion unit 38, passes through the antenna lines of the electrode 41. During the passage of the water vapor gas through the antenna lines, the water vapor gas is ionized (ionization) by a circular-arc-like electric field (indicated by a two-dot chain line in FIG. 4(B)) which is caused by an electromagnetic field induced by the linear antenna lines, to thereby generate hydroxide ions and electrons (e⁻), and these electrons (e⁻) are collided with the water vapor gas so that hydroxy (OH) radicals and oxygen (O) radicals are generated.

Next, an operation of the radical sterilization apparatus according to the present embodiment based on the aforesaid structure will now explained. Similar to each of the aforesaid embodiments, both a state of an air pressure and a state of water vapor gas in the storage means 1 are adjusted, and an alternating current supplied from the power supply portion 42 flows through the electrode 41 so that an electromagnetic field is generated around the antenna lines of the electrode 41 serving as an antenna. The water vapor gas can be forcibly supplied so as to pass in the vicinity of the conductive lines (antenna lines) of the electrode 41, which has a powerful magnetic field of the electromagnetic field, whereby it is possible to facilitate a radical formation in the water vapor gas due to the powerful magnetic field.

Other Embodiments of the Invention

Similar to the aforesaid second embodiment, a radical sterilization apparatus according to another embodiment of the present invention includes a storing means 1, a low air pressure maintaining means 2, a water vapor gas production means 3 and a radical generation means 4. An air pressure in the container of the storage means 1 is controlled by the low air pressure maintaining means 2 so that the air pressure at the water vapor gas production process is different from that at the electric discharge process, and these processes are cyclically carried out at an interval of a given time. During the generation of hydroxy (OH) radicals and oxygen (O) radicals, the air pressure in the container of the storage means 1 is controlled at an arbitrary value between 1 Pa and 100 Pa.

Like this, by setting the two different air pressure in the single airtight container forming the storage means 1, it is possible to carry out the generation of the water vapor gas and the generation of the hydroxy (OH) radicals and oxygen (O) radicals by the electric discharge at respective optimum pressures, whereby it is possible to more efficiently carry out the generation of the hydroxy (OH) radicals and oxygen (O) radicals by a simple arrangement of the apparatus.

Also, a radical sterilization apparatus according to yet another embodiment of the present invention is arranged in a similar manner to each of the aforesaid embodiments. In addition to each of the arrangements, a subject to be treated, stored in the storage means 1, is covered with a sheet, for example, a micro-mesh sheet and so on, through which the hydroxy (OH) radicals and oxygen (O) radicals can pass, but through which bacteria cannot pass, and the subject covered with the sheet is subjected to the sterilization process is carried out. Thus, when the subject is taken out of the storage means 1 after the sterilization process, it can be prevented from adhesion of bacteria.

Also, although the aforesaid second embodiment is arranged so that the water vapor gas pressure and the water vapor gas flow rate are individually adjusted, in a radical sterilization apparatus according to still yet another embodiment of the present invention, only one of the water vapor gas pressure and the water vapor gas flow rate may be adjusted and controlled.

The invention claimed is:

1. A radical sterilization apparatus comprising:
a storage means including an airtight container that stores a subject to be treated, which is to be subjected to a sterilization process;
a low air pressure maintaining means for maintaining a pressure in said storage means in a low pressure state;
a water vapor gas production means including a diffusion unit provided in the airtight container of said storage means for evaporating a liquid water, directly introduced into said airtight container in which the pressure is maintained in the low pressure state, by said diffusion unit, to thereby produce water vapor gas; and
a radical generation means including a linear electrode which is provided in said airtight container in the vicinity of said diffusion unit and between said diffusion unit and said subject to be treated, and which is bent so as to include linear sections which are in parallel with a longitudinal direction of said diffusion unit, so that the water vapor flows into clearances between the linear sections of said linear electrode, wherein an electric current is applied to said electrode in a water vapor ambiance created by said water vapor gas, to thereby cause electric discharge in the vicinity of the linear sections of the linear electrode so that hydrogen oxide of said water vapor gas, directed to said subject to be treated, is ionized to generate hydroxy (OH) radicals and oxygen (O) radicals.

2. The radical sterilization apparatus as set forth in claim 1, wherein an air pressure in the water vapor gas production in said water vapor gas production means is higher than an interior air pressure in the airtight container of said storage means, but it is lower than an atmospheric pressure.

3. The radical sterilization apparatus as set forth in claim 1, wherein said water vapor gas production means is integrally formed with and identical with the airtight container of said storage means.

4. The radical sterilization apparatus as set forth in claim 1, wherein said radical generation means is arranged so that a low pressure glow discharge is generated by said electrode with an electrical current supplied thereto.

5. The radical sterilization apparatus as set forth claim 1, wherein said radical generation means is driven so that said electrode is supplied with the alternating current at the frequency from 1 kHz to 10 kHz, and so that the alternating voltage from 7 kV to 13 kV is applied to said electrode.

6. The radical sterilization apparatus as set forth in claim 1, wherein the liquid water is directly introduced into the low air pressure container by using a small flow-rate variable needle valve.

7. The radical sterilization apparatus as set forth in claim 1, wherein said low air pressure maintaining means changes the pressure of the water vapor in the airtight container of said storage means from 1 Pa to 1,000 Pa.

8. The radical sterilization apparatus as set forth in claim 1, wherein the air pressure in the container of said water vapor gas production means is from 10 Pa to 10,000 Pa;

wherein the air pressure in the airtight container of said storage means is from 1 Pa to 1,000 Pa; and wherein the respective air pressures of said water vapor gas production means and storage means are proportionally increased and reduced.

9. The radical sterilization apparatus as set forth in claim 1, wherein the air pressure in an airtight container during production of the water vapor gas is higher than that in the airtight container during the electric discharge, and wherein the production of water vapor gas and the generation of hydroxy (OH) radicals and oxygen (O) radicals are alternately carried out.

* * * * *